United States Patent
Sexton

(10) Patent No.: US 8,214,031 B1
(45) Date of Patent: *Jul. 3, 2012

(54) SWITCH FOR TRANSDERMAL PATCH

(75) Inventor: Frederick A. Sexton, Rumson, NJ (US)

(73) Assignee: Purdue Pharma L.P., Stamford, CT (US)

( * ) Notice: Subject to any disclaimer, the term of this patent is extended or adjusted under 35 U.S.C. 154(b) by 36 days.

This patent is subject to a terminal disclaimer.

(21) Appl. No.: 12/130,458

(22) Filed: May 30, 2008

Related U.S. Application Data

(60) Provisional application No. 60/941,244, filed on May 31, 2007.

(51) Int. Cl.
*A61N 1/30* (2006.01)

(52) U.S. Cl. .................................................. 604/20

(58) Field of Classification Search .............. 604/131, 604/890.1, 19–22, 27, 28, 46, 48, 289, 290
See application file for complete search history.

(56) References Cited

U.S. PATENT DOCUMENTS

| | | | | |
|---|---|---|---|---|
| 4,314,554 A | * | 2/1982 | Greatbatch | 604/20 |
| 5,885,211 A | | 3/1999 | Eppstein et al. | |
| 5,983,130 A | | 11/1999 | Phipps et al. | |
| 6,136,839 A | | 10/2000 | Isakson et al. | |
| 7,141,034 B2 | | 11/2006 | Eppstein et al. | |
| 7,392,080 B2 | * | 6/2008 | Eppstein et al. | 604/20 |
| 2004/0204673 A1 | * | 10/2004 | Flaherty | 604/65 |
| 2008/0208107 A1 | * | 8/2008 | McRae et al. | 604/20 |

OTHER PUBLICATIONS

McRae et al., Transdermal Porator and Patch System and Method for Using Same, filed Jan. 22, 2007.*
Paul A. Insel, "Analgesic-Antipyretic and Antiflammatory Agents and Drugs Employed in the Treatment of Gout" in *Goodman & Gilman's The Pharmacological Basis of Therapeutics* (Perry B. Molinhoff & Raymond W. Ruddon eds., 9th ed. 1996), pp. 617-657.
Glen R. Hanson, "Analgesic, Antipyretic and Anti-Inflammatory Drugs" in *Remington: The Science and Practice of Pharmacy*, vol. II (A.R. Gennao e. 19th ed. 1995), pp. 1196-1221.
T.A. Peterson et al., "Design, Development, Manufacturing and Testing of Transdermal Drug Delivery Systems" in *Transdermal and Topical Drug Delivery Systems* (T.K. Ghosh et al. eds., 1997) pp. 249-297.
U.S. Appl. No. 12/130,410, Frederick Sexton: "Transdermal Patch", filed May 30, 2008, pending.
U.S. Appl. No. 12/130,496, Frederick Sexton "Transdermal Device Having Mechanical Assist for Porator-To-Skin Contact", filed May 30, 2008.
U.S. Appl. No. 12/131,508, Frederick Sexton "Transdermal Patch Packaging", filed Jun. 2, 2008, pending.
U.S. Appl. No. 12/167,966, Frederick Sexton "Dispenser for Transdermal Devices", filed Jul. 3, 2008, pending.

* cited by examiner

*Primary Examiner* — Jackie Ho
*Assistant Examiner* — Imani Hayman
(74) *Attorney, Agent, or Firm* — Leason Ellis LLP

(57) ABSTRACT

A transdermal device such as a patch can include a drug source, a porator, and an energy storage device on-board the patch. The porator operates free of any concurrent connection to any external source of power. A switch can be used to make the selective electrical connection between the porator and the energy storage device. The switch can be arranged to respond to a manual user action after the patch has been adhered to skin, including separation of the porator from a remainder of the patch. Optionally, a series of switches can make electrical connections between the porator and respective individual energy storage devices.

24 Claims, 7 Drawing Sheets

SWITCH FOR TRANSDERMAL PATCH

CROSS REFERENCE TO RELATED APPLICATIONS

This application claims the benefit of priority, under 35 U.S.C. §119(e), of U.S. Provisional Application Ser. No. 60/941,244, filed May 31, 2007, which is hereby incorporated by reference in its entirety.

FIELD OF THE INVENTION

This invention relates to transdermal devices, and, in particular, to a disposable transdermal device having on-board power for microporating skin.

BACKGROUND OF THE INVENTION

Transdermal drug delivery and monitoring systems are desirable in many circumstances in that self-administration by untrained persons is required. For example, transdermal drug patches are available commercially for curbing nicotine cravings due to smoking, as a birth-control aid, for pain relief, and a wide variety of specific applications. A principal benefit of transdermal drug delivery as compared to the historical use of injectable dosage forms is that it provides the drug directly to the blood stream without the discomfort of needles, lancets and other sharp instruments, and without the need for training in the use and disposal of such instruments. As compared to oral dosage forms, transdermal delivery can be more effective for some regimens when it is desirable to deliver a drug clear of the hostile environment presented by gastrointestinal juices or by first pass metabolism. Further, transdermal devices permit monitoring of blood components.

A popular form for transdermal drug delivery systems is a patch having an adhesive layer or perimeter suitable for adhering the patch to skin. A matrix containing a drug or a drug reservoir supplies the drug through the skin over a period of time such as several hours or days. Likewise, blood monitoring can be performed through the skin and into the patch. However, skin includes a layer known as the stratum corneum that is chiefly responsible for the barrier properties of skin to prevent transdermal flux of drugs or other molecules into the body and of analytes out of the body. The stratum corneum has a thickness of about 10 to about 40 microns and is continuously renewed by shedding of corneum cells during desquamation and the formation of new corneum cells by a keratinization process. For some drugs, such as opiates, the stratum corneum can impede significant flux, and so it is desirable to overcome this barrier to enable a wider array of topical and transdermal delivery systems.

It is generally desirable to enhance transdermal drug delivery and blood monitoring, and in this regard there are several known methods for increasing the permeability of skin to drugs. Among these is a methodology known as "microporation" or "poration," which refers to the formation of a hole or crevice (defined herein as a "micropore") in a biological membrane, such as skin or mucous membrane, of a patient. The micropore lessens the barrier properties of the skin to the passage of drugs into the patient for a therapeutic treatment, or of biological fluids out of the patient for analysis. The micropore can range from about 1 to about 1000 microns in diameter and typically extends into the skin sufficiently so as to reduce the barrier properties of the stratum corneum without adversely affecting the underlying tissues. Typically, multiple micropores are created in a single application of this methodology. See, for example, U.S. Pat. Nos. 5,885,211 and 7,141,034 (the '034 patent) for a description of various thermal and electrical microporation techniques and devices.

In order to create micropores, energy is applied to the skin surface. In the '034 patent, that energy is provided either by a hand-held external device or from a self-contained unit that combines a transdermal delivery device with an energy source. The devices proposed by the '034 patent are multi-part assemblies, which appear to be cumbersome and awkward to use. It would be preferable to have a light-weight, flexible transdermal device that is electrically chargeable and fully disposable as compared to the assemblies described in the '034 patent. Alternatively, there are disposable transdermal patches with chemical reservoirs that can be mixed together to create an exothermal reaction, which might be made suitable for creating a micropore; however, the chemicals required and their associated reactions introduce substantial complexities into the manufacture of the transdermal device.

Accordingly, there remains a need for improved methods and devices for the transdermal delivery of agents such as drugs, and for the monitoring of analytes such as blood components. The present invention concerns transdermal delivery devices of this nature.

SUMMARY OF THE INVENTION

In accordance with one aspect of the present invention, a transdermal device is provided with an on-board switch which is connected between an energy storage device and a porator. The switch makes selective electrical connection to the porator to porate the skin. The switch can be arranged to respond to a manual user action after the patch has been adhered to skin.

In another aspect of the invention, any of the transdermal devices described herein can include a set of chargeable energy storage devices and associated switches. Each energy storage device can be serially connectable to a porator so as to discharge any stored charge in said energy storage device and thereby actuate the porator. A set of switches connects the porator to a respective energy storage device in the set of chargeable energy storage devices. Closure of any given switch in the set of switches makes the connection between the respective energy storage device and the porator.

In accordance with yet another aspect of the present invention, a transdermal patch can comprise the following features. A drug source for transdermal delivery of a drug through a skin of a user and a dermal contact layer positioned to maintain the drug source in contact with the skin. A removable carrier supports an electrically-actuatable porator. The porator is removably seated so as to substantially or completely overlie the drug source. An on-board energy storage device suitable for storing an electric potential is supported for selective electrical connectivity to the porator. Conductive contact terminals extend from the energy storage device for connection to an external source of power. The external source of power couples the electric potential and stores it in the energy storage device. As a result of this structure, the porator is actuatable by connection to the on-board energy storage device, and will perform its function free of any concurrent connection to any external source of power.

In a further aspect according to the above arrangement, the removable porator can be configured to have the selective connection of the energy storage device to the porator be established in response to removal of the carrier from its seat. Also, the porator can be initially seated so as to overlie at least a portion of the drug source and thereby be proximate to the skin prior to its removal. The porator and its carrier can be separated from the transdermal patch, leaving behind a remainder portion comprising the transdermal contact layer and the drug source.

In accordance with still another aspect of the invention, a transdermal patch can comprise the following features. A drug source for transdermal delivery of a drug through a skin of a user, an electrically-actuatable porator, and a dermal contact layer positioned to maintain the drug source and the porator in contact with the skin, as described above. The porator can be disposed in a non-removable arrangement relative to the drug source. An energy storage device suitable for storing an electric potential is supported for selective electrical connectivity to the porator. Conductive contact terminals extend from the energy storage device for connection to an external source of power. The external source of power couples the electric potential and stores it in the energy storage device. As a result of this structure, the porator is actuatable by connection to the on-board energy storage device and will perform its function free of any concurrent connection to any external source of power.

In certain embodiments, a mechanical bias is supported in a transdermal device of the invention so as to apply a displacement force to a rear surface of the porator, thereby increasing the likelihood of adequate physical contact between the porator and the skin. The mechanical bias can assume a stable mechanical state, or the bias can apply a positive pressure that urges the porator into more intimate contact with the skin, or both.

These and other aspects, features and advantages will be apparent from a review of the Drawing Figures and the accompanying discussion of certain embodiments of the invention.

BRIEF DESCRIPTION OF THE DRAWING FIGURES

DETAILED DESCRIPTION OF CERTAIN EMBODIMENTS OF THE INVENTION

The present invention provides improvements in transdermal delivery of agents such as drugs to a user, and monitoring of analytes such as blood components absorbed transdermally from a user. A transdermal device in accordance with the invention includes a dermal contact adhesive for affixation to the skin of a user, as is conventional, and further includes circuitry for microporating the skin. The circuitry communicates electrically with an on-board energy storage device, which comprises a portion of a single-use, disposable transdermal device. The energy storage device stores a charge sufficient to activate one or more porator elements, and more typically one or more arrays of porator elements, included in the microporator circuitry in order to disrupt the stratum corneum. Contact terminals extend from the energy storage device and provide an electrical connection between the energy storage device and an external power source. Preferably a switch provides manual control as to the exact moment (s) that the porator is to be activated and can be constructed from portions of the device that can be removed, leaving behind a remainder that stays adhered to the skin.

Figure 1A:
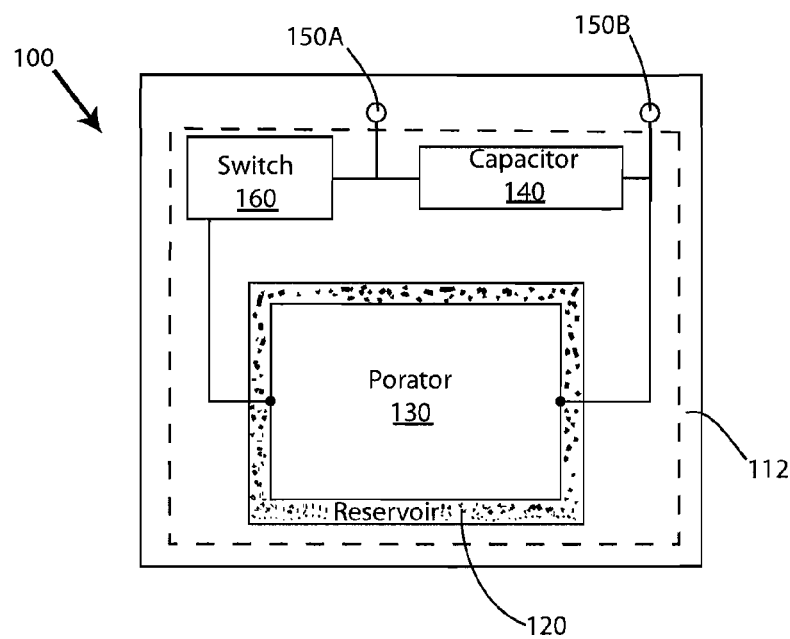
FIG. 1A is a schematic view of an embodiment of a transdermal device in accordance with the invention in a first arrangement in which a porator is separable from the transdermal device.
Figure 1B:
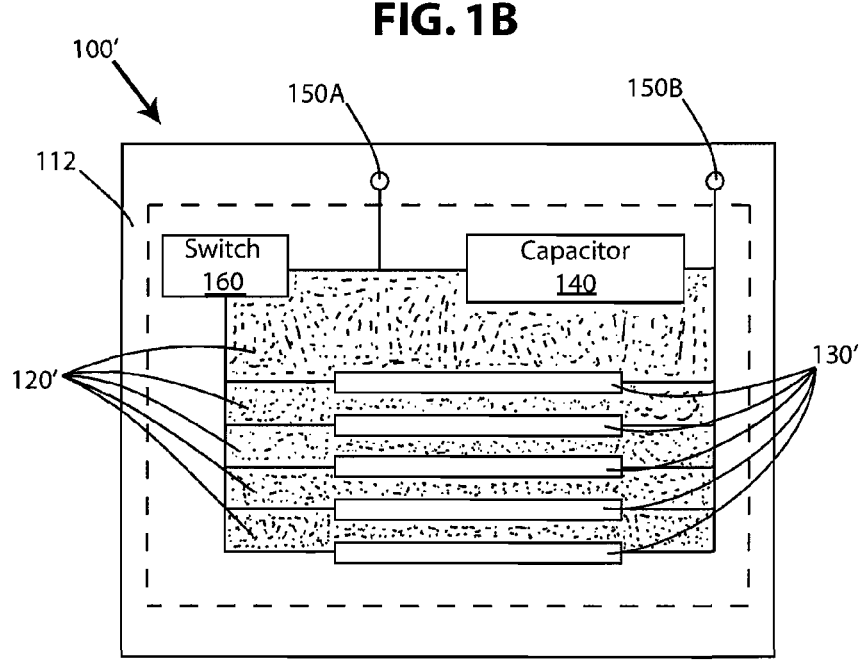
FIG. 1B is a schematic view of the embodiment of FIG. 1A showing an alternative arrangement in which a porator is integral with the transdermal device.

Depending on the construction of the transdermal device, the porator element itself can remain a part of the transdermal device after poration of the skin is achieved, or it can be separated from the transdermal device. Referring now to FIGS. 1A and 1B, two non-limiting arrangements of a transdermal device are illustrated in the form of transdermal patches 100, 100'. Both patches include a flexible dermal contact layer with an adhesive 112 arranged, for example, around their perimeters for securing to skin of a user. The compliant portions of the dermal contact layer 110 (see FIG. 2C) are intended to conform to the shape of and attach to the skin surface. Optionally, the dermal contact layer 100 can flex to accommodate any displacement of the layers that comprise the patches 100, 100' without slippage relative to the skin, particularly in embodiments that include a mechanical bias element which applies pressure to improve porator-skin contact. The dermal contact layer may comprise one or more compounds such as, but not limited to, an acrylic, silicone rubber, latex, vinyl, polyurethane, plastic, polyethylene or the like. The dermal contact layer supports the drug source 120, 120' included on the patch 100, 100', respectively, in position relative to the skin. Suitable adhesives 112 for attachment of the dermal contact layer 110 to the skin surface may include any one of the large number of existing, medical grade adhesives used in bandages, dressings, and transdermal patches currently being produced. Many manufacturers, such as 3M, Avery, Specialty Adhesives, and the like, manufacture adhesives that can be useful in this type of application.

Still referring to FIGS. 1A and 1B, the porator 130 is a component, or is the entirety, of the microporator circuitry and is situated so as to have a front surface in abutting contact with the skin after the patch has initially been affixed to the user and an opposing rear surface that can be supported on a removable or stationary carrier. In the arrangement of FIG. 1A, the porator 130 is separable from the patch 100, as described in more detail below. By separating the porator, the drug source can occupy a substantial portion of the contact between the skin and the patch 100. In the arrangement of FIG. 1B, the drug source 120' and the porator 130' are shown interspersed along a surface of the patch 100'. In alternative layout arrangements, the porator can surround or partially surround the drug source 120'. Regardless of its surface layout, the porator 130' is integral to the construction of the patch 100'. The porator can comprise an appropriate resistive element such as, e.g., a tungsten, tantalum, or tungsten alloy. The porator can be constructed as described in aforementioned U.S. Pat. No. 7,141,034. It is preferred that the surface area of skin porated by the porator generally coincide with the portion of the patch 100, 100' that delivers the drug source.

A drug source 120 can take the form of a matrix, a reservoir, or plurality thereof, and is disposed on the patch so that the drug source is in abutting contact with the skin after the patch has been affixed to the user. Examples of transdermal patches that are suitable for use with drug sources that comprise pain relief compositions, as in preferred embodiments of the invention, include: (1) the matrix-type patch; (2) the reservoir-type patch; (3) the multi-laminate drug-in-adhesive type patch; (4) the monolithic drug-in-adhesive type patch; and (5) hydrogel patch. See generally Ghosh, T. K.; Pfister, W. R.; Yum, S. I. Transdermal and Topical Drug Delivery Systems, Interpharm Press, Inc. p. 249-297, which is hereby incorporated by reference. These patch constructions are well known in the art and are available commercially. Regardless of the construction selected for a given patch construction, the drug source preferably remains sealed as long as the patch is in its packaging prior to use. The drug source can be sealed within a liquid-impermeable cover, which can be removed when the patch is ready for use. One example of a liquid impermeable-cover is the porator carrier 132, described below in connection with FIGS. 2 and 3.

As used herein, "reservoir" refers to a designated storage area or chamber within the transdermal device. The reservoir can be designed to contain a drug for delivery through the skin of a user. Alternatively, the reservoir can be designed to receive a biological fluid sample from the skin of the user. A reservoir may further comprise one or more excipients typically associated with transdermal delivery devices. Alternatively, a reservoir may further comprise one or more reagents designed to enable the measurement or detection of a selected analyte in an absorbed biological fluid. Where a drug is to be delivered to the user through the skin, the reservoir serves as a drug source and comprises a viscous liquid, a gel or a porous polymer comprising a selected drug for release into the skin of the user. Where the reservoir is designed to receive a biological fluid sample from the user for subsequent analysis, the reservoir serves as a sink to absorb the biological fluid sample, and comprises a viscous liquid, a gel or a porous polymer adapted for absorption of the biological fluid sample.

As used herein, a "matrix" refers to refers to a portion or the entirety of the skin-contacting surface of the transdermal device which includes a drug for delivery through an artificial opening in a biological membrane into an organism or which receives a biological fluid sample extracted from an organism through an artificial opening in a biological membrane, as described above. A matrix could contain, or be treated with any of the excipients or reagents that a reservoir could contain. In one arrangement, the adhesive 112 can overlie a substantial portion or all of the matrix. The drug matrix can be of two types: the drug-in-adhesive system and the matrix dispersion system. In the drug-in-adhesive system, the drug is disposed in an adhesive polymer and then the so-medicated polymer adhesive is spread, for example, by solvent casting or by melting the adhesive (in the case of hot-melt adhesives), onto an impervious backing layer. Layers of unmedicated adhesive polymer can be applied on top of the medicated polymer layer. In the case of the matrix dispersion system, the drug is dispersed homogeneously in a hydrophilic or lipophilic polymer matrix and fixed onto a drug-impermeable backing layer. The adhesive can be applied as a peripheral adhesive as shown in FIGS. 1A and 1B.

More generally, the matrix or reservoir(s) include a permeant, that is, a first material that permeates another material (skin). The permeant can be one or more agents such as drugs or for monitoring analytes such as blood components.

Both patch arrangements will include at least one on-board energy storage device 140, illustrated here as a capacitor. Alternatively, the energy storage device can be a chemical cell that is energizable so as to store an electric potential suitable for activating the microporator circuitry. Contact terminals 150A, 150B are in electrical contact with respective positive and negative terminals of the storage element 140. For example, one of the contact terminals can be connected to ground potential while the other is connected to a higher potential, such as 1 Volt to 12 Volts, D.C. In this manner, power can be supplied to the contact terminals from an external source in order to place the transdermal patch in a "ready-to-microporate" state prior to affixation to the skin and free of any connection to an external or bulky power source. Thus, the microporating circuitry on board the patch will receive power from an external power source, yet the external power source is not required when the porator is actuated.

Figure 2A:
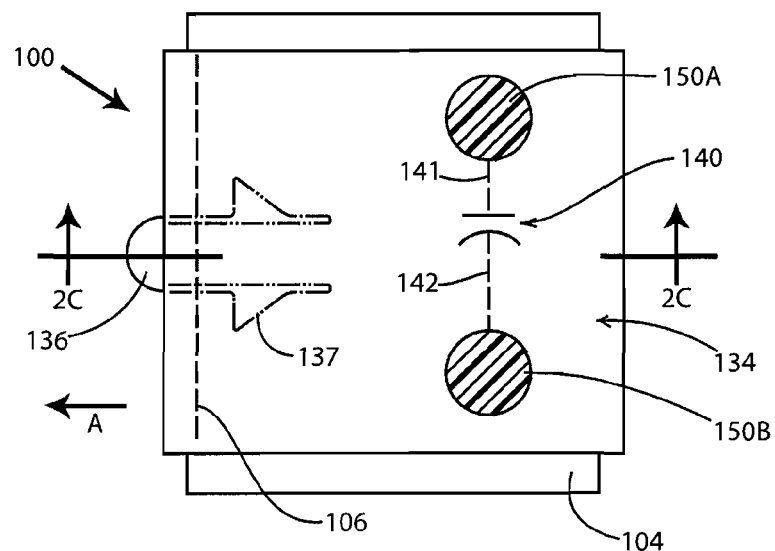
FIG. 2A is a top plan view illustrating a transdermal device according to the arrangement of FIG. 1A.

Optionally, the contact terminals 150A, 150B communicate with conductive tracings of a packaging that surrounds and seals (and possibly hermetically seals) the patch 100, 100' until ready for use. The contact terminals 150A, 150B can thus be disposed on a surface of the transdermal device (as shown in FIG. 2A) so as to make electrical contact with respective conductive tracings provided on an interior of the packaging and thereby transfer electric potential to the energy storage device 140 while the patch remains protected in the packaging. Suitable packaging that can transfer an electric potential to the patch 100, 100' is described in co-pending U.S. Application Ser. No. 60/941,157, filed on even date herewith, entitled "Transdermal Patch Packaging," which is hereby incorporated by reference in its entirety. This arrangement enables power to be supplied through the packaging in order to place the transdermal patch in a "ready-to-microporate" state prior to opening the package.

Figure 4A:
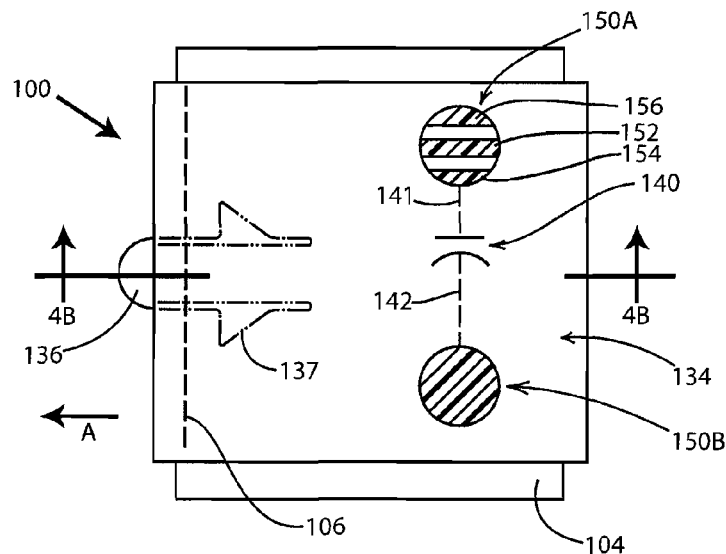
FIG. 4A is a top plan view illustrating a transdermal device according to the arrangement of FIG. 1A, but comprising multiple energy storage devices, which can be individually charged and discharged.
Figure 4B:
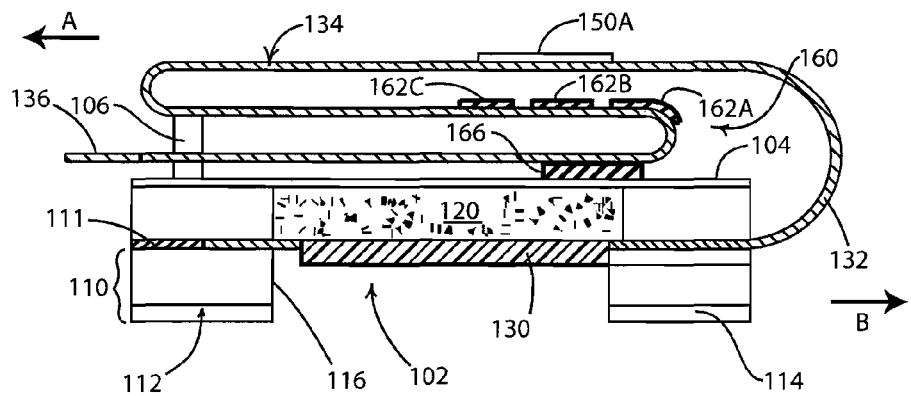
FIG. 4B is a cross-section taken along line 4B-4B of FIG. 4A.
Figure 4C:
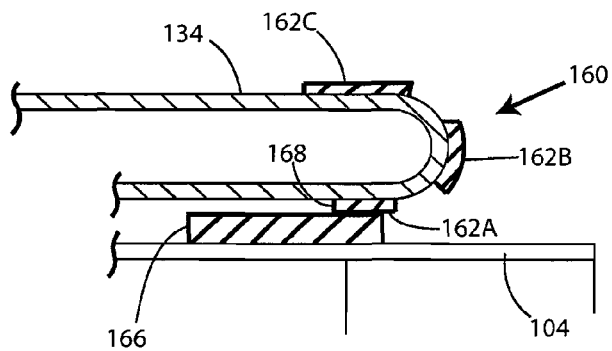
FIG. 4C is a detail view of a portion of a series of manually-actuated switches included with the transdermal device of FIG. 4A.
Figure 4D:
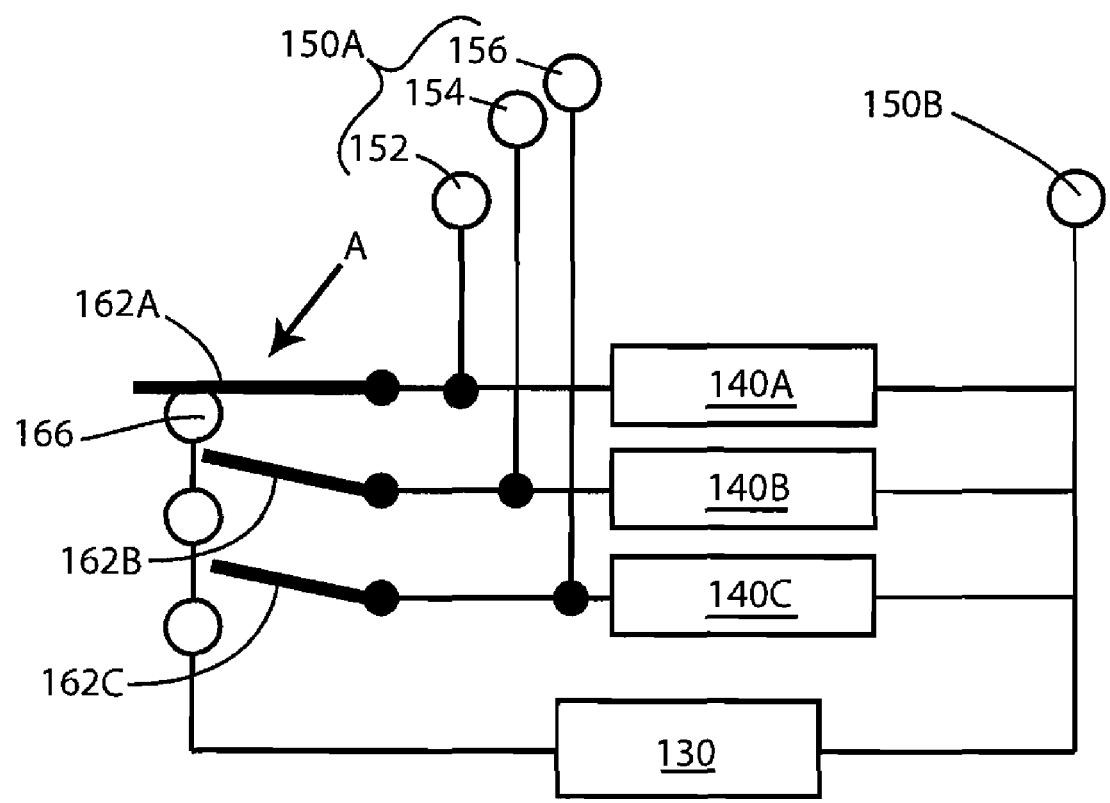
FIG. 4D is a circuit schematic of the switch of FIG. 4C.

Turning briefly to FIGS. 4A and 4D, the patch 100 (or equivalently patch 100') optionally can be provided with plural energy storage devices 140 (e.g., 140A, 140B, 140C, etc.) which can be energized through the terminals 150A, 150B. One of the terminals 150A, 150B can be common to all energy storage devices; in FIG. 4D, terminal 150B is connected to each of several energy storage devices. The other terminal 150A should comprise plural contacts, each contact being in electrical communication with a respective one of the energy storage devices; in FIG. 4D, terminal 150A comprises contacts 152, 154, and 156, and these contacts connect to the energy storage devices 140A, 140B, 140C, respectively. As described above, terminals 150A, 150B can be arranged so as to engage conductive tracings provided on an interior of a surrounding packaging. As will be apparent from the discussion below, by dividing terminal 150A into plural contacts, the plural contacts can be simultaneously connected to a source of power for simultaneous charging of each separate storage device 140A, 140B, 140C, etc. while permitting each storage device to be individually and separately discharged when the patch is affixed to the skin and the poration mechanism actuated. Such an arrangement permits a staggered series of separate poration events or "pulses," which can be effective in creating more permeable micropores.

The stored electric potential is releasable from the storage element 140 after the patch has been adhesively mounted on the skin so as to create micropores in the region of the drug source 120, 120'. Release of the stored electric potential is in response to the closing of a switch 160, which as described below includes a stationary contact 166 and a movable contact 162. Preferably, the switch is manually actuated by a user at a desired moment after the patch has been mounted. The switch can have any one of a variety of forms, as described below, but a preferred arrangement has the switch constituted by parts that are already to be moved in order to displace the porator and expose the drug source (in embodiments that have a displaceable porator). Once actuated, the action of the porator creates micropores of about 1 to about 100 microns across and about 10 to about 50 microns deep so as to improve the delivery of drug to the user or the absorption of analyte from the user across the stratum corneum.

Figure 2B:
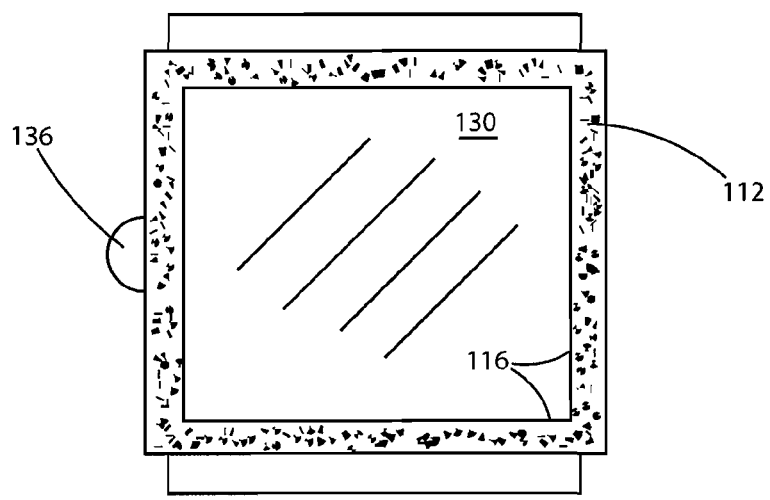
FIG. 2B is a bottom plan view of the transdermal device of FIG. 2A.
Figure 2C:
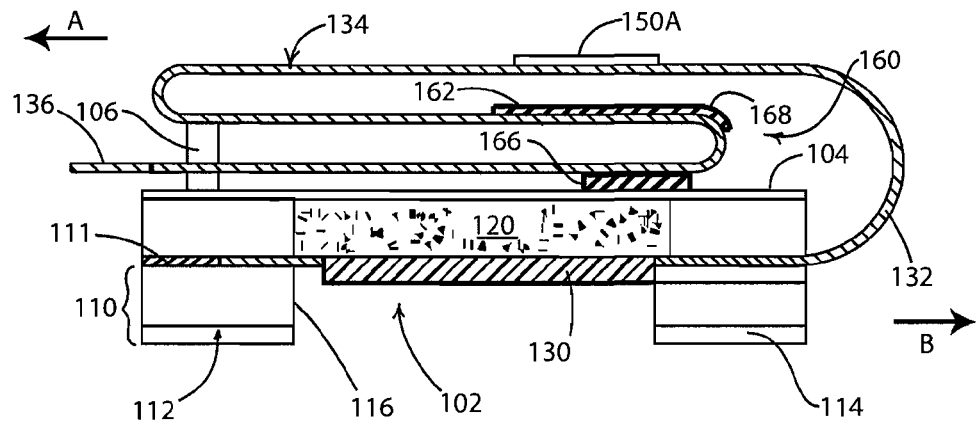
FIG. 2C is a cross-section taken along line 2C-2C of FIG. 2A.

One embodiment of a transdermal patch 100 having a removable porator 130 is illustrated in FIGS. 2A, 2B and 2C. The porator 130 can be seated in register with a window 102 defined by walls 116 of the dermal contact layer 110, as shown in FIG. 2B. A removable liner 114 (FIG. 2C) can overlie the dermal adhesive 112 (as shown), or can comprise a part of the packaging for the patch. The dermal contact layer can also include a laminated layer 111 on an opposite side thereof for joining to the drug source 120.

The porator can comprise a Thin Film Tissue Interface (TFTI) device that creates micropores using thermal energy produced by the passage of electrical current through resistive elements, as described in U.S. Pat. No. 7,141,034 of Eppstein et al., which is hereby incorporated by reference in its entirety. TFTI devices can create one or more micropores on a wide range of biological membranes. TFTIs are characterized by their ability to rapidly and efficiently create a pattern or array of micropores on the surface of a biological membrane. The pattern may be any geometric spacing of micropores with pore densities as high as one pore every 0.2 square mm and covering a total porated area ranging from a few square millimeters to easily include the surface area of the entire patch, if desired. TFTI devices are designed to be thin, flexible, conformable structures. Disposable transdermal devices of the present invention can use TFTI devices without a sophisticated controller because each poration element or electrode or other active component (such as a piezotransducer) in the TFTI can be provided with an identical drive signal, in parallel to other porators in an array, to porate the skin beneath the transdermal device in response to a single discharge of energy from the on-board energy storage device. Conveniently, the drive signal can be a current provided in a discharge loop that includes the energy storage device(s) 140.

The porator serves as a heat source to raise the temperature of a small area of tissue, typically about 1 to 1000 micron in diameter, to greater than about 123° C., preferably greater than about 400° C., which is then followed by a return to ambient skin temperature within a total cycle time of about 1 to about 50 microseconds so as to minimize both collateral damage to adjacent tissues and any painful sensation to the user. The time of energy application is a function of the discharge rate from the energy storage device and the length of time the energy is being applied to the porator through the closed switch 160. The result of this application of thermal energy is a vapor-driven removal of corneocytes in the stratum corneum. Sufficient energy will thus form a micropore preferably through the stratum corneum and down to the next layer of the epidermis, which is the stratum lucidum.

Still referring to FIGS. 2A, 2B and 2C, the porator 130 is supported on a carrier 132 which preferably includes a top panel 134 and a tab 136. The top panel supports the contact terminals 150A, 150B that are electrically connected to respective terminals of the energy storage device 140. The tab 136 is preferably sized for grasping by a user. The top panel 134 and tab 136 can be an integral part of the carrier 132. The top panel 132 can be secured to a top surface 104 of the patch 100 by a breakable seal 106. The seal can comprise a perforated connection to the top surface 104 or an adhesive bond. The force required to pull the tab can be greater than the force required to break seal 106 so that the top panel 134 remains attached until a user intends to separate the porator from the patch. Optionally, the tab can include features such as wings 137 which, upon withdrawal of the tab in the direction of arrow A, bear against the seal 106 from below the top panel and assist in breaking the seal.

The carrier 132 can also support the energy storage device 140, as shown in FIG. 2A. The energy storage device can take the form of a thin film capacitor or a fuel cell, both of which are two-terminal storage devices. Regardless of the form of the energy storage device or which of the elements of the transdermal patch 100, 100' support it, a pair of conductive leads 141, 142 extend from the energy storage device to respective contact terminals 150A, 150B.

Figure 2D:
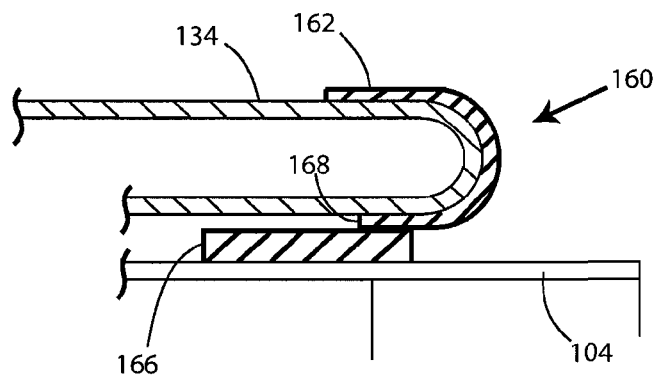
FIG. 2D is a detail view of a portion of a manually-actuated switch included with the transdermal device of FIG. 2A.
Figure 2E:
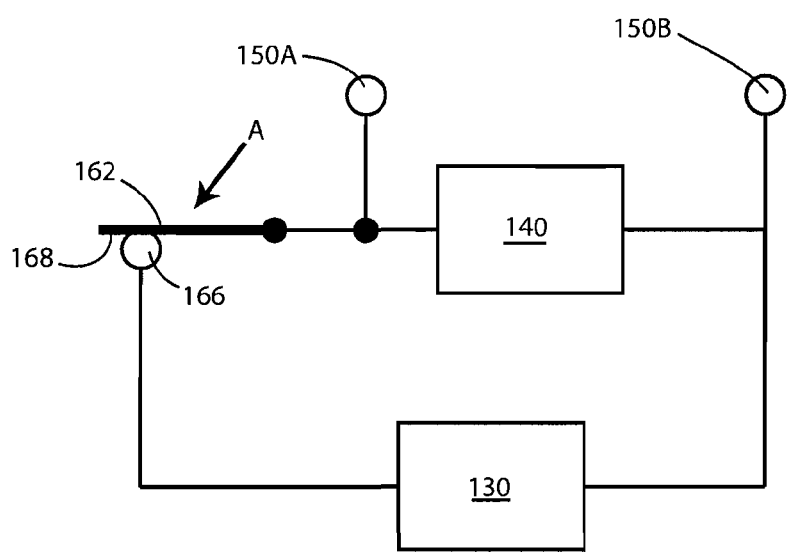
FIG. 2E is a circuit schematic of the switch of FIG. 2D.

Referring now to FIGS. 2C, 2D and 2E, an embodiment of a switch 160 is described. As illustrated, the tab 136 is withdrawn in the direction of arrow A which moves a conductive arm 162 into electrical contact with pole 166. When the tab is in a rest position as shown in FIG. 2A, the seal 106, if provided, is unbroken and a leading conductive edge 168 of the arm 162 is spaced from pole 166. In this state, the porator is part of an open circuit and not actuated. Meanwhile, the arm 162 is in conductive contact with a circuit node that connects to contact 150A (as shown). As the tab moves in the direction of arrow A, the leading edge 168 advances into contact with the pole 166 while the arm 162 remains electrically connected to the circuit node that includes contact 150A. Continued movement of the tab 136 causes a leading edge of the arm 162 to advance to the position shown in FIG. 2D at which the arm 162 contacts the pole 166. Such contact completes a series circuit which includes the porator 130, as shown schematically in FIG. 2E. The switch 160 is closed to actuate the porator and thereby discharge a current through the porator. In one embodiment, the switch closure is in response to movement of at least a portion of the carrier, namely, the tab 136. Discharge of substantially all of the stored charge can be instantaneous in embodiments which utilize a capacitor as the energy storage device, and electrical contact can be made or maintained until the tab has been moved beyond the trailing edge of the arm 162. The porator is intended for single-use, and once it has discharged it can be removed from the patch, as described below.

Where there are multiple porators forming a porator array in a single patch, preferably the porator array is connected in parallel for simultaneous application of the charge in the energy storage device 140 to all of the porators. The power requirement to deliver sufficient energy to the array to raise the temperature of the skin under the array can be determined in view of the number of porator elements and size of each porator in the array, their respective resistances, the duration of energy application (e.g., about 1 millisecond) and consideration of the extreme current handling capabilities of the porators (e.g., 40 Amperes). Based on these parameters, an energy storage device 140 can be selected with sufficient capacity to drive the porator array to achieve its intended purpose.

Once the porator has been used to disrupt the stratum corneum, the porator can be removed from a remainder of the patch 100.

Referring now to FIGS. 4B, 4C, and 4D, the switch 160 in this embodiment comprises plural conductive arms 162A, 162B, 162C that cooperate with the stationary pole 166 to complete respective series circuits that provide energy to the porator 130. As illustrated, the tab 136 is withdrawn in the direction of arrow A which moves the series of conductive arms 162A, 162B and 162C into serial electrical contact with stationary pole 166. When the tab is in its initial rest position, as shown in FIG. 4B, the seal 106, if provided, is unbroken and the first conductive arm 162A in the series is spaced from the stationary pole 166. In this position, the porator is part of an open circuit and has not yet been actuated. Meanwhile, the arm 162A is in conductive contact with a circuit node that connects to contact 152 (as shown). Likewise, in this rest position the conductive arms 162B and 162C are spaced from the pole 166 and are in conductive contact with a circuit node that includes contacts 154, 156, respectively. As the tab moves in the direction of arrow A, the leading edge 168 (see FIG. 4C) advances into contact with the pole 166 while the arm 162 remains electrically connected to the circuit node that includes contact 150A. Continued movement of the tab 136 causes the leading edge 168 to advance to the position shown in FIG. 4C at which the arm 162A contacts the pole 166. This contact completes a series circuit which includes the porator 130 and the energy storage device 140A, as shown schematically in FIG. 4D. The switch including arm 162A is closed to actuate the porator 130 using the energy in energy storage device 140A and thereby discharge a first current through the porator 130 by movement of at least a portion of the carrier, namely, the tab 136. Discharge continues until the tab has been moved beyond the trailing edge of the arm 162A, and can be expected to last on the order of about 1-millisecond.

The length of time that the switch remains closed and the porator can receive energy varies with the length of the arm 162 along the tab 136 of the carrier, and the pull speed by the user in the direction of arrow A. The time of energy application is a function of the discharge rate from the energy storage device and the length of time the energy is being applied to the porator by a closed switch 160, but generally can be instantaneous if the energy storage device is a capacitor. In the arrangement of FIGS. 4A-4D, additional porator actuations can be achieved without movement of the transdermal device 100, 100' relative to the skin, without the use of an external power source, and without the need for a logic circuit or processor to control the timing of energy delivery. Rather, the arrangement shown in FIGS. 4A-4D provides additional conductive arms 162B, 162C, which are each electrically connectable to the porator 130 so as to close respective circuits and apply energy from separate energy storage devices 140B, 140C, respectively. While three conductive arms and three associated energy storage devices are illustrated, fewer or additional conductive arms and associated energy storage devices can be provided, as desired.

With further reference to FIGS. 4B and 4C, as the tab 136 continues to move in the direction of arrow A, the conductive arms 162B and 162C serially engage the stationary pole 166, closing respectively in sequence additional circuits, and thereby sequentially applying energy from energy storage devices to the porator 130. Each respective circuit closes when and while the conductive arms 162A, 162B, 162C are in contact with the stationary pole 166.

FIG. 4D illustrates schematically the conductive arm 162A closing a first energy delivery circuit that supplies energy to the porator 130 for discharge of heat into the skin. The circuit is closed because the conductive arm 162A is in contact with stationary pole 166, which is the position illustrated in FIG. 4C. Meanwhile, conductive arms 162B and 162C remain spaced away from the stationary pole, as illustrated schematically as open circuits in FIG. 4D. With continued movement of the tab 136 in the direction of arrow A, the circuit including energy storage device 140A opens and shortly thereafter the circuit including energy storage device 140B closes. Each closure of the switch 160 results in an actuation of the porator 130 and a release of thermal energy into the skin. These multiple deployments of energy can be effective in disrupting or reducing the barrier imposed by the stratum corneum with lower amounts of energy being applied with each circuit closure than if only a single energy deployment were used. As a result, the user can experience reduced discomfort or sensation from the poration of skin using a transdermal device configured as illustrated in FIGS. 4A-4D.

The timing between the opening of one circuit and the closing of the next is partially a function of the spacing between the conductive arms 162, and also a function of the rate that the user pulls the tab 136. Of interest, however, is that a staggered, time-release of energy can be achieved mechanically, without the use of an integrated circuit. Further, such an energy release is in response to a simple manual movement, such as the pulling of the tab 136. As a consequence of this unique solution, a fully disposable transdermal device can be manufactured which is simple for a user to use.

In the embodiments illustrated in FIGS. 1A, 2C, and 4B, removal of the porator after actuation provides unobstructed contact between the drug source 120 and the skin of the user through the window 102. Because of the micropore disruption of the stratum coreum, the patch can beneficially include a smaller quantity of drug than conventional patches because drug flux into the skin is enhanced. Additionally, or in the alternative, the creation of micropores beneficially ensures that substantially all of a drug transfers from the patch to the user, leaving little or no drug residue in the patch, which is particularly desirable for patches containing certain controlled substances.

Figure 3A:
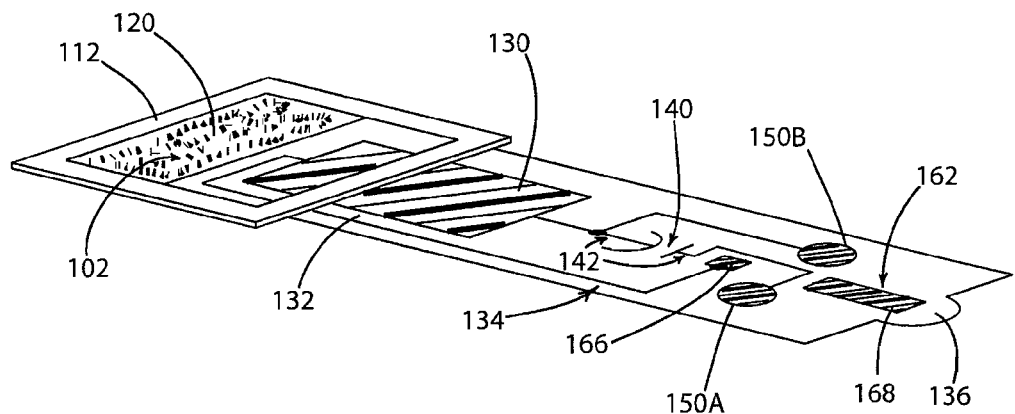
FIG. 3A is a perspective view of FIG. 2B, now illustrating the porator partially withdrawn from the transdermal device.
Figure 3B:
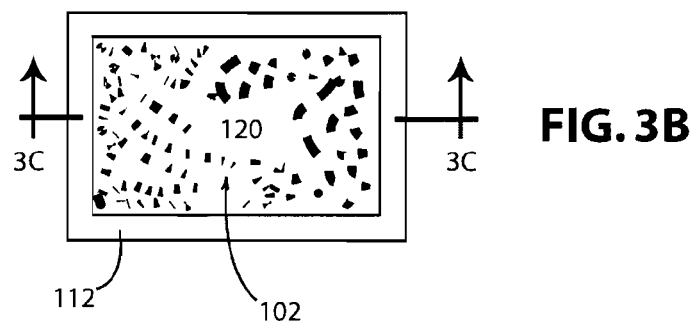
FIG. 3B is the top plan view of FIG. 3A, now illustrating the drug source fully exposed after the porator has been completely separated therefrom.
Figure 3C:
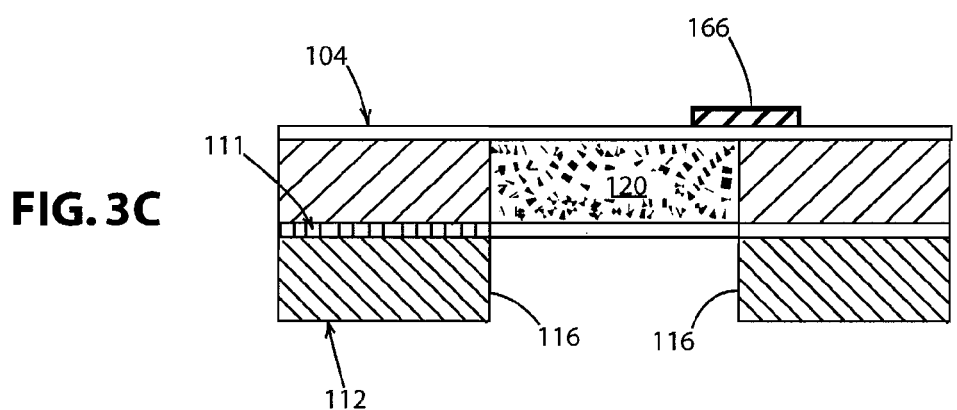
FIG. 3C is a cross-section taken along line 3C-3C of FIG. 3B showing a configuration of the transdermal device after removal of the porator and its carrier.

Referring now to FIG. 3A, the carrier 132 of the illustrated embodiment is shown partially separated from the patch. In FIG. 3A, the tab 136 has already been fully extended to close the circuit and actuate the porator 130 and the top panel 134 has already been pulled in the direction of arrow A and has been partially pulled in the direction of arrow B (see also FIG. 2C). As a result, the carrier 132 and the porator 130 are partially withdrawn from the window 102 to thereby permit the drug source 120 to contact skin through the window 102. The patch can be mounted to the user's skin, for example, using the dermal adhesive 112 that surrounds the window 102, and in other arrangements such as those in which a matrix is used as the drug source 120, the drug or other permeant can permeate the skin through the dermal contact layer 110 (FIG. 2C) and adhesive 112 without requiring a window. Continued pulling of the tab 136 fully withdraws the porator 130, leaving behind that portion of the transdermal device shown in FIG. 3B. The patch can remain on the user's skin for a period of time ranging from minutes to days, depending on the purpose and instructions for any particular patch. After removal of the porator 130 and carrier 132, the portion of the transdermal device remaining on the skin can have a configuration as shown in the cross-section of FIG. 3C.

Figure 3D:
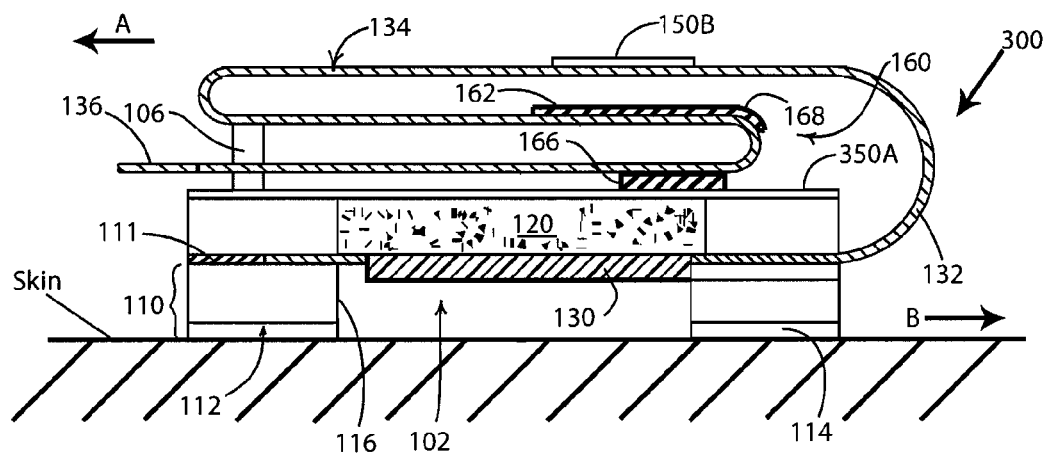
FIG. 3D is a cross-section taken along the line 2C-2C of FIG. 2A showing an optional bias that can be included with the transdermal device in a rest position.
Figure 3E:
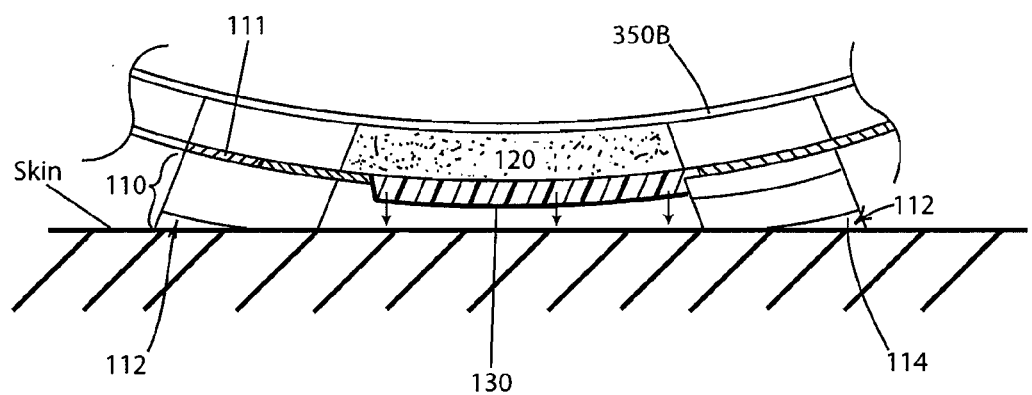
FIG. 3E is the cross-section of FIG. 3D, now showing the bias in an active position in which it applies positive pressure to the porator to urge it into more intimate contact with skin.

FIGS. 3D and 3E illustrate a passive bias mechanism that can be provided on the transdermal device to better ensure positive contact between the porator 130 and the user's skin. In FIG. 3D, the transdermal device 300 is a modification of the device of FIG. 2A so as to include a mechanical bias element 350 that can impart a bias in the direction of the skin once the device is mounted onto the skin. In FIG. 3D, the mechanical device 350 is in a rest position 350A, and the adhesive 112 is in adhering contact with the user's skin. FIG. 3D exaggerates the distances to illustrate the benefit of the bias mechanism 350. In particular, after mounting the transdermal device 300 to the skin, a portion or all of the porator 130 may not make adequate or optimal physical contact with the skin, and this is undesirable because the porator will not be as effective in porating the skin. In FIG. 3E, the mechanical bias element is shown as it moves toward an activated position 350B, such as can be the result of a user pressing upon the transdermal device 300 after mounting to skin and before activating the porator circuit (e.g., by pulling the tab 136). In the activated position, the bias mechanism 350 flexes into a stable configuration in which it urges the porator 130 into contact with the skin (as shown by the motion arrows) and maintains such contact. Meanwhile, the material of the dermal contact layer 110 flexes so as to accommodate the force applied by the mechanical bias element 350 while the adhesive 112 remains firmly in adhesive contact with the skin. In this embodiment, once in the activated position (not shown), the porator 130 can make more adequate physical contact with the skin across the entire surface of the porator 130. The mechanical bias element can comprise a bias such as made from metal or plastic. The bias should have a rigidity that is sufficient to maintain its activated position 350B as a stable state after being depressed by the user. Because the bias is a passive mechanism, it can be implemented in a simple manner as part of a disposable transdermal device.

Referring again to FIGS. 1B and 2C and as noted above, a patch 100' can be configured to have a porator 130' which is integral to the patch itself. In this arrangement, the patch 100' can have a window 102 for delivering a stored energy to the porator 130' and a drug via a drug source 120', or for absorbing and monitoring an analyte as described above. Alternatively, the drug in the drug source 120 can be contained in a matrix and can permeate the skin through the dermal contact layer 110 and adhesive 112 without requiring a separate window 102. In the patch 100', the electrically-actuatable porator 130' can surround, partially surround, or be interspersed with the drug source 120', but in this embodiment the porator is integrated into the patch so that it is not removable. The porator 130' can be located on or within the substrate that contains the drug source 120'. Thus, the substrate can be a non-conductive material that supports conductive traces that contact at crosspoints to define an array of simultaneously activated microporators. The traces can comprise fibers that are part of a weave supported by the substrate, or a deposited conductive material, or a preformed wire conductor, or a machined conductive material. Optionally, ends of the microporator(s) can be free to move as the porator wires/fibers/elements increase in length with the rapid increase in temperature. Optionally, the microporator(s) can self-destruct during use to prevent reuse, such as by being provided with a current beyond the wire's capacity, or by being mounted so that the porator structure mechanically fails during thermal expansion of the material of the wire (e.g. such as where the wires are rigidly mounted and break under expansion stress, or are mounted to a tearable substrate that yields to the expansion stress).

Just as described above, the embodiment of FIG. 1B can include conductive contacts 150A, 150B that extend from the energy storage device 140 for connection to an external source of power. The external source of power couples the electric potential and stores it in the energy storage device. A switch 160 provides manual control over the timing of when the energy storage device discharges its charge. The switch 160 can comprise the arrangement substantially as described above in connection with FIG. 2A-2E or 4A-4D, except that the porator 130' is not removable in this embodiment, or can comprise a different switch arrangement. The switch that is used is part of the microporator circuit and enables that circuit to be completed (i.e., to enable a closed loop to be formed which applies the terminals of the energy storage device 140 to the porator's terminals). The switch can comprise a depressible arm on one portion of the patch that contacts an underlying, stationary pole mounted on another part of the patch, or a peelable element that places two circuit points into conductive contact with each other (or peels away an insulative spacer to permit other elements to move into conductive contact with one another, or can be a switch that responds to the environment (e.g., oxygen or light) by changing its state so as to permit conduction suitable to energize the porator.

The porator 130, 130' transforms the skin into a high efficiency transport state by disrupting the stratum corneum, and as such a transdermal device including a porator, an on-board energy storage device and contact terminals to pre-charge the energy storage device for disposable use can be used in the delivery of a wide variety of drugs and agents, including those having molecular weights in the range of about 300 to about 40,000 daltons.

The terms "agent" and "drug" are used interchangeably herein and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and anti-viral agents, analgesics and analgesic combinations, anesthetics, anxiolytics, anorexics, anti-arthritics, anti-asthmatic agents, anti-convulsants, anti-depressants, anti-diabetic agents, anti-diarrheals, antihistamines, anti-inflammatory agents, anti-migraine preparations, anti-motion sickness preparations, anti-nauseants, anti-neoplastics, anti-parkinsonism drugs, anti-pruritics, anti-psychotics, anti-pyretics, anti-spasmodics including gastrointestinal and urinary anti-spasmodics, anti-cholinergics, sympathomimetrics, xanthine derivatives, cardiovascular preparations including calcium channel blockers, beta-blockers, anti-arrythmics, anti-hypertensives, diuretics, vasodilators including general, coronary, peripheral and cerebral vasodilators, central nervous system stimulants, cough and cold preparations, decongestants, diagnostics, hormones, hypnotics, immunosuppressives, muscle relaxants, parasympatholytics, parasympathomimetrics, proteins, peptides, polypeptides, antibodies, antibody fragments, and other macromolecules, psychostimulants, sedatives and tranquilizers.

The therapeutic agent can be an opioid agonist, a non-opioid analgesic, a non-steroidal anti-inflammatory agent, an antimigraine agent, a Cox-II inhibitor, a 5-lipoxygenase inhibitor, an anti-emetic, a $\beta$-adrenergic blocker, an anticonvulsant, an antidepressant, a Ca2+-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating addictive disorder, an agent for treating Parkinson's disease and parkinsonism, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for inhibiting vomiting, an agent for treating dyskinesia, an agent for treating depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic and Anti-inflammatory Agents and Drugs Employed in the Treatment of Gout, in Goodman & Gilman's The Pharmacological Basis of Therapeutics* 617-57 (Perry B. Molinhoff and Raymond W. Ruddon eds., 9$^{th}$ ed 1996); and Glen R. Hanson, *Analgesic, Antipyretic and Anti-Inflammatory Drugs in Remington: The Science and Practice of Pharmacy Vol II* 1196-1221 (A. R. Gennaro ed. 19$^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

In the foregoing description, certain features have been described in relation to certain embodiments of the invention, but these same features are to be understood as being useable in other arrangements and embodiments. Accordingly, the invention is defined by the recitations in the claims appended hereto and equivalents thereof, and is not limited to particular details of any of the foregoing embodiments that rather are provided to facilitate an understanding of the invention and to satisfy certain statutory requirements.

I claim:

1. A transdermal patch having an on-board energy storage device for coupling to an external power source in order to store a charge in the energy storage device, comprising:
    a dermal contact layer having an adhesive suitable for securing the dermal contact layer to a skin of a user;
    a drug source supported by the dermal contact layer for transdermal delivery of a drug through the skin of the user;
    an electrically-actuatable porator disposed so as to substantially or completely overlie the drug source;
    a removable carrier, wherein the porator is supported by the carrier and is removable therewith, the porator being removable by a pulling movement from a rest position in which the porator substantially or completely overlies the drug source to a second position;
    the chargeable energy storage device being selectively electrically connectable to the porator so as to discharge the stored charge and thereby actuate the porator; and
    a switch connected between the energy storage device and the porator for making the selective electrical connection to the porator, the switch comprising a stationary pole and an arm mounted for movement by the user relative to the pole.

2. The transdermal patch of claim 1, further comprising conductive contact terminals extending from the energy storage device, the contact terminals being connectable to the external power source so as to couple an electric potential from the external power source and store the charge in the energy storage device.

3. The transdermal patch of claim 1, wherein the arm is mounted on the carrier and wherein the selective connection of the energy storage device to the porator is made in response to movement of at least a portion of the carrier.

4. The transdermal patch of claim 1, wherein the carrier is severally affixed to the transdermal patch so as to be severable therefrom.

5. The transdermal patch of claim 1, further comprising at least one electrically-insulative layer.

6. The transdermal patch of claim 5, wherein the energy storage device is supported on the at least one electrically insulative layer.

7. The transdermal patch of claim 1, wherein the energy storage device is supported on either the drug source or the dermal contact layer.

8. The transdermal patch of claim 1, wherein the porator comprises at least one pair of spaced electrodes supported for contact with the skin of the user.

9. The transdermal patch of claim 1, wherein the energy storage device comprises a capacitor.

10. The transdermal patch of claim 1, wherein the drug source comprises a matrix or at least one drug reservoir.

11. A transdermal patch having a set of on-board energy storage devices for coupling to an external power source in order to store a charge in each of the energy storage devices, comprising:
- a dermal contact layer having an adhesive suitable for securing the dermal contact layer to a skin of a user;
- a drug source supported by the dermal contact layer for transdermal delivery of a drug through the skin of the user;
- an electrically-actuatable porator disposed so as to substantially or completely overlie the drug source;
- a pullingly moveable carrier supporting the porator;
- each energy storage device being serially, electrically connectable to the porator with movement of the carrier so as to discharge in serial manner first the stored charge in one of said energy storage devices in the set and then another of said energy storage devices in the set and thereby actuate the porator multiple times with continued movement of the carrier; and
- a set of switches, each switch being connected between the porator and a respective energy storage device in the set of chargeable energy storage devices, whereby closure of any given switch in the set of switches makes the connection between the respective energy storage device and the porator.

12. The transdermal patch of claim 11, further comprising conductive contact terminals extending from each energy storage device in the set of chargeable energy storage devices, the contact terminals being connectable to the external power source so as to couple an electric potential from the external power source and store the charge in all of the energy storage devices.

13. The transdermal patch of claim 11, further comprising a removable carrier, wherein the porator is supported by the carrier and is removable therewith, the porator being removable from a rest position in which the porator substantially or completely overlies the drug source to a separated position in which the porator is remote from the drug source.

14. The transdermal patch of claim 13, wherein each switch comprises a stationary pole and a moveable arm, wherein all of the moveable arms are mounted on the carrier and wherein the selective connection of the porator to each energy storage device in the set of chargeable energy storage devices is made in response to movement of at least a portion of the carrier so as to serially connect to the porator one energy storage device in the set of chargeable storage devices after another.

15. The transdermal patch of claim 13, wherein the carrier is severally affixed to the transdermal patch so as to be severable therefrom.

16. The transdermal patch of claim 11, further comprising at least one electrically-insulative layer.

17. The transdermal patch of claim 16, wherein the set of chargeable energy storage devices is supported on the at least one electrically insulative layer.

18. The transdermal patch of claim 11, wherein the set of chargeable energy storage devices is supported on either the drug source or the dermal contact layer.

19. The transdermal patch of claim 11, wherein the porator comprises at least one pair of spaced electrodes supported for contact with the skin of the user.

20. The transdermal patch of claim 11, wherein the set of chargeable energy storage devices comprise respective capacitors.

21. The transdermal patch of claim 11, wherein the drug source comprises a matrix or at least one drug reservoir.

22. A transdermal patch having an on-board energy storage device for coupling to an external power source in order to store a charge in the energy storage device, comprising:
- a dermal contact layer having an adhesive suitable for securing the dermal contact layer to a skin of a user;
- a drug source supported by the dermal contact layer for transdermal delivery of a drug through the skin of the user;
- an electrically-actuatable porator disposed so as to substantially or completely overlie the drug source;
- wherein the chargeable energy storage device being selectively electrically connectable to the porator so as to discharge the stored charge and thereby actuate the porator;
- a switch connected between the energy storage device and the porator for making the selective electrical connection to the porator, the switch comprising a stationary pole and an arm mounted for movement by the user relative to the pole; and
- an elongate flexible carrier configured to be movable relative to the drug source and the stationary pole,
- wherein the arm is supported by the elongate flexible carrier and movable therewith so that movement of the elongate flexible carrier relative to the drug source and the stationary pole causes the arm to electrically contact the stationary pole to energize the electrically-actuatable porator.

23. The transdermal patch of claim 1, wherein the carrier is pullingly moveable to discharge the stored charge free of any concurrent connection to the external power source.

24. The transdermal patch of claim 11, wherein the carrier is pullable to discharge in serial manner the stored charge in each said energy storage device free of any concurrent connection to the external power source.

* * * * *